United States Patent [19]

Ario et al.

[11] Patent Number: 5,554,030
[45] Date of Patent: Sep. 10, 1996

[54] METHOD FOR BONDING NON-AMALGAM RESTORATIVE MATERIALS TO DENTAL SURFACES

[75] Inventors: Paula D. Ario, Minneapolis; Steven M. Aasen, Woodbury, both of Minn.

[73] Assignee: Minnesota Mining and Manufacturing Company, St. Paul, Minn.

[21] Appl. No.: 268,773

[22] Filed: Jun. 30, 1994

[51] Int. Cl.⁶ ............................. A61C 5/04; A61C 5/00
[52] U.S. Cl. ........................................ 433/226; 433/228.1
[58] Field of Search .................................. 433/218, 219, 433/226, 228.1

[56] References Cited

U.S. PATENT DOCUMENTS

| | | |
|---|---|---|
| 3,513,123 | 5/1970 | Saffir . |
| 3,574,943 | 4/1971 | Stark et al. . |
| 3,882,600 | 5/1975 | Plymale . |
| 4,001,483 | 1/1977 | Lee, Jr. et al. ............ 526/270 |
| 4,064,629 | 12/1977 | Stoner et al. . |
| 4,182,035 | 1/1980 | Yamauchi et al. ......... 433/228 |
| 4,235,633 | 11/1980 | Tomioka et al. ........... 106/35 |
| 4,251,565 | 2/1981 | Bowen .................... 433/226 |
| 4,259,117 | 3/1981 | Yamauchi et al. ......... 106/35 |
| 4,368,043 | 1/1983 | Yamauchi et al. ......... 433/217 |
| 4,383,052 | 5/1983 | Higo . |
| 4,499,251 | 2/1985 | Omura et al. ............. 526/278 |
| 4,515,930 | 5/1985 | Omura et al. ............. 526/276 |
| 4,535,102 | 8/1985 | Kusumoto et al. ........ 523/116 |
| 4,537,940 | 8/1985 | Omura et al. ............. 526/278 |
| 4,539,382 | 9/1985 | Omura et al. ............. 526/276 |
| 4,540,722 | 9/1985 | Bunker .................... 523/109 |
| 4,544,467 | 10/1985 | Bunker et al. ............ 204/159.24 |
| 4,669,983 | 6/1987 | Bunker .................... 433/217.1 |
| 4,719,149 | 1/1988 | Aasen et al. .............. 433/226 X |
| 4,830,616 | 5/1989 | Okuda ..................... 433/217 |
| 4,872,936 | 10/1989 | Engelbrecht .............. 156/307.3 |
| 4,880,660 | 11/1989 | Aasen et al. .............. 433/226 X |
| 4,929,746 | 5/1990 | Bunker .................... 558/92 |
| 5,141,436 | 8/1992 | Orlowski et al. .......... 433/226 |
| 5,256,447 | 10/1993 | Oxman et al. ............. 427/207.1 |
| 5,264,513 | 11/1993 | Ikemura et al. ........... 526/318 |
| 5,276,068 | 1/1994 | Waknine .................. 522/28 |

FOREIGN PATENT DOCUMENTS

| | | |
|---|---|---|
| 0058483 | 8/1982 | European Pat. Off. . |
| 0237233 | 9/1987 | European Pat. Off. . |
| 0234934 | 9/1987 | European Pat. Off. . |
| 0348718 | 1/1990 | European Pat. Off. . |
| 0408357 | 1/1991 | European Pat. Off. . |
| 0423430 | 4/1991 | European Pat. Off. . |
| 0609902 | 10/1994 | European Pat. Off. . |
| 0661034 | 5/1995 | European Pat. Off. . |
| 2561521 | 9/1985 | France . |
| 2739282 | 2/1978 | Germany . |
| 57-143372 | 9/1982 | Japan . |
| 57-167364 | 10/1982 | Japan . |
| 63-175085 | 7/1988 | Japan . |
| 63-250310 | 10/1988 | Japan . |
| 2261223 | 12/1993 | United Kingdom . |
| WO93/12790 | 8/1993 | WIPO . |

OTHER PUBLICATIONS

Abstract; Derwent Publications Ltd., London, Mitsui Petrochem Ind KK Jul. 2, 1985.
International Search Report.
M. Staninec and M. Holt, *Journal of Prosthetic Dentistry* (1988), vol. 59, pp. 397–402.
A. Lacey and M. Staninec, *Quintessence International* (1989), vol. 20, pp. 521–524.
Y. Torii et al. *Operative Dentistry* (1989), vol. 14, pp. 142–148.
CRA Newsletter; Adhesives, Silver Amalgam, (Feb. 1994).
Y. Aboush and C. Jenkins, *Br. Dent. J.* (1989), vol. 166, pp. 255–257.
Y. Aboush and R. Elderton, *Br. Dent. J.* (1991), vol. 170, pp. 219–222.
Y. Aboush and R. Elderton, *Dent. Mater.* (1991), vol. 7, pp. 130–132.
A. Ben–Amar, *J. Am. Dent. Assoc.* (1989), vol. 119, pp. 725–728.
M. Mitrosky, Jr., *Quintessence International* (1981), vol. 9, pp. 871–874.
H. J. Staehle et al., *Dtsch. Zahnartzt* (1988), vol. 43, pp. 952–957.
M. Buonocore, W. Wileman, and F. Brudevold, *J. Dent. Res.*, 35, 846 (1956).
M. Buonocore and M. Quigley, *J. Amer. Dent. Assoc.*, 57, 807 (1958).
M. Anbar and E. Farley, *J. Dent. Res.*, 53, 879 (1974).
E. Farley, R. Jones, and M. Anbar, *J. Dent. Res.*, 56, 943 (1977).

*Primary Examiner*—Nicholas D. Lucchesi
*Attorney, Agent, or Firm*—Gary L. Griswold; Walter N. Kirn; Dale A. Bjorkman

[57] ABSTRACT

A method for adhering non-amalgam dental restorative materials to a dental surface comprising the steps of a) etching the dental surface with acid, b) applying a treatment composition comprising an electron donor to the etched dental surface, c) applying a priming solution containing a film-former to the treated dental surface, d) applying a chemically curable dental adhesive to the primed dental surface, and e) applying non-amalgam dental restorative material to the adhesive-coated dental surface. The treatment composition comprises an electron donor compound selected such that the dental restorative has a higher Adhesive Shear Bond Strength than a like method without said electron donor compound.

16 Claims, No Drawings

“5,554,030”

METHOD FOR BONDING NON-AMALGAM RESTORATIVE MATERIALS TO DENTAL SURFACES

FIELD OF THE INVENTION

The present invention relates to bonding of non-amalgam restorative materials to dental surfaces. More specifically, the present invention relates to multiple-step procedures for bonding non-amalgam dental restorative materials to hard tissue, set amalgam or other surfaces of the oral environment.

BACKGROUND OF THE INVENTION

U.S. Patent No. 5,276,068 to Waknine discloses dental compositions useful for bonding dental surfaces, including enamel, dentin, porcelain and metallic surfaces, comprising polycarbonate dimethacrylate condensation products as a principle component, and a secondary monomer such as BIS-GMA or polyurethane dimethacrylate or the like as a second component, which is provided to impart strength to the dental composition. Also described therein are methods for bonding dental restorative materials to an exposed dentin surface, wherein the surface can be pretreated by application of 3% $H_2O_2$, 17% EDTA, or 5% NaOCl in non-vital teeth followed by an alcohol or acetone solution of an alkali metal salt of benzenesulfinic acid with subsequent evaporation of the alcohol from the solution. Alternatively, the surface can be pretreated by first applying an alcohol or acetone solution of an alkali metal salt of benzenesulfinic acid and then applying an acetone solution of N-phenylglycine. The treated dentin surface is then coated with a resinous adhesive. The adhesive is then cured and an appropriate dental restorative material is applied.

SUMMARY OF THE INVENTION

The present invention provides a method for adhering non-amalgam dental restorative materials to a dental surface comprising the steps of a) etching the dental surface with acid, b) applying a treatment composition comprising an electron donor to the etched dental surface, c) applying a priming solution containing a film-former to the treated dental surface, d) applying a chemically curable dental adhesive to the primed dental surface, and e) applying non-amalgam dental restorative material to the adhesive-coated dental surface, wherein the treatment composition comprises an electron donor compound selected such that the dental restorative has a higher Adhesive Shear Bond Strength than a like method without said electron donor compound.

DETAILED DESCRIPTION

The present invention offers distinct advantages to the dental patient for receiving comparatively low cost and low trauma dental care. With the present method of bonding non-amalgam restorative materials to various dental surfaces, the dentist can perform repairs using a low cost material with which he or she is familar. These repairs can now be made with substantially less preparation than required previously.

Additionally, the present method allows bonding of non-amalgam dental restorative materials to dental surfaces other than tooth structure that previously could not be repaired using these materials without complete removal of prior dental work. The present method bonds non-amalgam dental restorative materials to previously placed amalgam, metal (such as in pins, posts, and bridgework), glass ionomers, porcelain, previously placed composite restorations, or other materials used in the oral environment.

Generally, before the present method is carried out, the area of the oral cavity to be worked on is prepared using conventional dental techniques. For example, hard tissue (e.g. enamel or dentin) to which the non-amalgam dental restorative material is to be applied preferably is first cleaned using conventional methods (e.g., by abrading it with a bur), rinsed (e.g., using water) and dried (e.g., using air).

In the first step of the present method, the dental surface is etched with acid. An appropriate acid etch technique may be used to provide a surface receptive to bonding materials thereto.

Acids for use in the acid etch step can be inorganic or organic acids, and if organic can be monomeric, oligomeric or polymeric. If desired, a precursor to the acid such as an acid anhydride, e.g., 4-Methacryloxyethyl Trimellitate Anhydride (4-META), acid halide (including inorganic acid halides such as Lewis acids, e.g., ferric chloride, and organic acid halides), or ester can be used in place of the acid itself, e.g., to generate the desired acid in situ. Suitable acids include mineral acids, carboxylic acids, sulfonic acids, and phenols, with carboxylic acids, alkylsulfonic acids, arylsulfonic acids, and phosphonic acids being preferred.

The acid has a pKa in water that is less than or equal to that of phenol. Preferably, the pKa of the acid is between about −20 and about +10, more preferably between about −10 and about +5.

Suitable inorganic acids include HBr, HCl, and $HNO_3$. Suitable organic acids include acetic acid, α-chloropropionic acid, 2-acrylamido-2-methylpropane sulfonic acid, acrylic acid, benzenesulfonic acid, benzoic acid, bromoacetic acid, 10-camphorquinone-sulfonic acid, 10-camphorsulfonic acid, chloroacetic acid, citraconic acid, citric acid, dibromoacetic acid, dichloroacetic acid, di-HEMA ester of 1,2,4,5 benzenetetracarboxylic acid, 2,4-dinitrophenol, formic acid, fumaric acid, 2-hydroxy-4-methoxybenzophenone-5-sulfonic acid, maleic acid, methacrylic acid, 2-naphthalene sulfonic acid, nitric acid, oxalic acid, p-nitrophenol, phenol, phosphoric acid, phosphorous acid esters (such as 2,2'-bis(α-methacryloxy-β-hydroxypropoxyphenyl) propane diphosphonate (Bis-GMA diphosphonate), dibutyl phosphite, di-2-ethylhexyl phosphate, di-2ethylhexyl phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), pivalic acid, propionic acid, sulfuric acid, toluene sulfonic acid, tribromoacetic acid, trichloroacetic acid, trifluoroacetic acid, trifluoromethanesulfonic acid, and trihydroxybenzoic acid. Mixtures of such acids can be used if desired.

Where the dental surface to be bonded to is dentin, preferably the acid does not generate insoluble salts of calcium during the etch technique in an amount that would detrimentally affect adhesion to the oral surface. If the acid does generate insoluble calcium salts, the salts are preferably rinsed from the dental surface before subsequent steps are taken.

Under typical conditions, the dental surface to be bonded is first exposed to about 0.01–0.2 ml of acid solution for a period of about 5–60 seconds. Preferred etching solutions contain about 10% maleic acid or about 35% phosphoric acid. Generally, the higher the acid strength and concentration, the shorter the time of exposure to the acid solution required to achieve the desired effect. This acid may be applied with dropper sponge or brush. The acid solution may optionally be dried on the dental surface by, e.g. air. Preferably, no drying step is taken after acid etch.

After the dental surface is etched with acid, a treatment composition comprising an electron donor is applied to the etched dental surface. The donor has an $E_{ox}$ greater than zero and less than or equal to $E_{ox}$(p-dimethoxybenzene). Preferably $E_{ox}$ (donor) is between about 0.5 and 1 volts vs. a saturated calomel electrode ("S.C.E."). $E_{ox}$ (donor) values can be measured experimentally, or obtained from references such as N. L. Weinburg, Ed., *Technique of Electroorganic Synthesis Part II Techniques of Chemistry*, Vol. V (1975), and C. K. Mann and K. K. Barnes, *Electrochemical Reactions in Nonaqueous Systems* (1970).

Preferred donors include ascorbic acid, metal complexed ascorbic acid, cobalt (II) chloride, ferrous chloride, ferrous sulfate, hydrazine, hydroxylamine, oxalic acid, thiourea, tertiary amines (such as N,N-bis-(2-hydroxyethyl)-p-toluidine, 4-(dimethylamino)-phenethyl alcohol and the like), and aromatic salts of a dithionite, thiosulfate, or sulfite anion.

A preferred electron donor is the aromatic sulfinate salt represented by the general formula

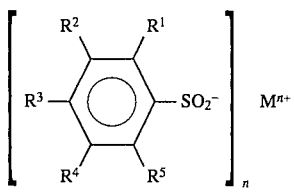

wherein $R^1$, $R^2$, $R^3$, $R^4$ and $R^5$ may be any atoms and/or groups as long as they are inert to the double bond of monomers. Examples are hydrogen, fluoro, chloro, bromo, iodo, methyl, ethyl, 2-chloroethyl, 2-bromo-2-chloroethyl, propyl, isopropyl, per-fluoropropyl, allyl, butyl, isobutyl, sec-butyl, tert-butyl, pentyl, isopentyl, neopentyl, tert-pentyl, cyclohexyl, phenyl and 4-bromophenyl.

$M^{n+}$ is a cation with mono-valency to 4-valency that can, as a counter ion for sulfinic acid anion, form the sulfinate. Examples of $M^{n+}$ are alkali metal ions, such as $Li^+$, $Na^+$, $K^+$, and $Cs^+$, alkaline earth metal ions, such as $Be^{2+}$, $Mg^{2+}$, $Ca^{2+}$, $Sr^{2+}$ and $Ba^{2+}$, transition metal ions such as $Cr^{2+}$, $Cr^{3+}$, $Mn^{2+}$, $Fe^{2+}$, $Fe^{3+}$, $Co^{2+}$, $Co^{3+}$, $Ni^{2+}$, $Cu^{2+}$, $Zn^{2+}$, $Rh^{3+}$, $Pd^{2+}$, $Ag^+$, $Cd^{2+}$, $Ir^{3+}$, $Ir^{4+}$, and $Hg^{2+}$, and ammonium ions, such as $NH_4^+$, $(CH_3CH_2)_3NH^+$,

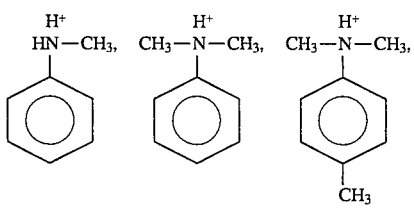

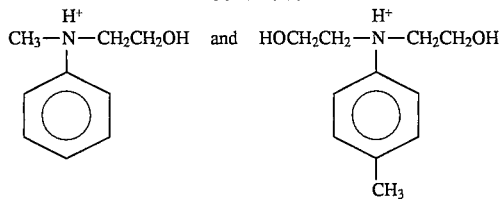

Preferred counter ions among these ions are $Li^+$, $Na^+$, $K^+$, $Mg^{2+}$, and $Ca^{2+}$, since sulfinates thereof have good stability when stored in monomers and have good solubility in the monomers.

Particularly preferred aromatic sulfinate salts include sodium benzenesulfinate and sodium toluenesulfinate. Optionally, the treatment composition may comprise mixtures of more than one aromatic sulfinate salt.

The electron donor is preferably provided in an appropriate solvent, such as water, acetone, lower alkyl alcohols (such as methanol, ethanol, propanol), and the like.

Optionally the treatment composition containing the electron donor may comprise other adjuvants, such as polymerization catalysts, medicaments, fluoride compounds, indicators, dyes, wetting agents, buffering agents, thixotropes and the like.

The treatment composition preferably comprises at least 0.1% by weight of electron donor, more preferably between 0.5 and 15, and most preferably between one and 10%. The treatment composition may be applied by any appropriate means, such as by dropper, sponge or brush. This composition is preferably allowed to reside on the etched surface for about 1–60 seconds.

The treatment composition is optionally dried on the surface with air, or the solvent is allowed to evaporate. After the treatment composition comprising an electron donor is applied to the etched dental surface, a priming solution containing a film-former is applied to the treated dental surface. For purposes of the present invention, a film-former is defined as a composition capable of forming a hardenable (e.g., polymerizable) continuous or semicontinuous film on the dental surface.

The film-former used in the primer of the present invention is preferably a water-dispersible substance or water-dispersible mixture of substances, such substance(s) being organic monomers, oligomers, polymers, or cosolvents. Most preferably, the film former contains at least one polymer prior to application to the treated dental surface. As used herein, a "water-dispersible" film former has a water dispersibility or more preferably a water solubility (exclusive of any water that may be present in the film former) of at least about 5 weight percent. Most preferably, the film former can be mixed with water in all proportions. For brevity, dispersible and soluble will sometimes be referred to collectively as dispersible. As used herein, "solubility" means the capability of a substance to form a solution, i.e., either a true solution or a colloidal solution. A true solution being a uniformly dispersed mixture at the molecular or ionic level, of one or more substances (the solute) in one or more substances (the solvent). These two parts of a solution are called phases. A colloidal dispersion is often called a solution. Since colloidal particles are larger than molecules it is strictly incorrect to call such dispersions solutions; however this term is widely used in the literature. As used herein, "dispersibility" means the capability of a substance to form a dispersion, i.e., a two-phase system where one phase consists of finely divided particles (often in the colloidal size range) distributed throughout a bulk substance, the particles being the disperse or internal phase and the bulk substance the continuous or external phase.

Preferred film formers contain one or more substances having a sufficient number of water-dispersing groups such as hydroxyl groups, carboxyl groups, sulfonic acid groups, cationic salts (e.g., ammonium, phosphonium or sulfonium groups), amide linkages or polyether linkages to render the film former water-dispersible. The film former, prior to removal of any volatile components, preferably wets the dental surface and most preferably has a sufficiently low viscosity to enable it to flow into interstices that already exist in the dental surface or that are created therein by the action of the acid. After removal of any volatile components, the film former preferably has a sufficiently high viscosity to enable it to resist displacement by dentinal fluids (in the case where the dental surface is dentin) or other extraneous liquids. The film former preferably contains one or more polymerizable substances. Addition polymerizable substances (e.g., vinyl compounds such as acrylates and methacrylates) are especially preferred.

Suitable preferred polymer components in the film former include linear, branched or cyclic polymers formed prior to priming of the treated dental surface. For purposes of this invention, a polymer is a chemical compound having at least two repeat units. They can be polymers of ethylenically unsaturated monomers or they can be polymeric compounds like polyester, polyamide, polyether, polyethyleneglycol, polyethyleneglycol dimethacrylate and diacrylate, polysaccharide, cellulosic, polypropylene, polyacrylonitrile, polyurethane, poly(vinyl chloride), poly(methyl methacrylate), phenol-formaldehyde, melamine-formaldehyde, and urea-formaldehyde. Mixtures of such polymers can be used if desired.

Preferred polymers are the polymers of ethylenically unsaturated monomers. These polymers may be homo- or co-polymers and may contain hydrophilic or hydrophobic groups. The polymer may optionally contain acid groups, their salts, or their reactive derivative groups. Particularly preferred polymers contain reactive groups that further react (i.e., crosslink or copolymerize) with the other components of the film former or the dental adhesive. Addition polymerizable reactive groups (e.g., vinyl groups such as acrylates and methacrylates) are especially preferred. Polymers of ethylenically unsaturated monomers are often used in dental glass ionomer cements. These polymers are especially useful in the present invention as they generally have good biocompatibility, are dispersible in water and have a suitable molecular weight. Particularly preferred polymers contain functional groups that have an affinity for hard tissue. For example, such groups include β-dicarbonyl groups and carboxylic acid groups. The polymer component of an ionomer cement is often a copolymer of acrylic acid and itaconic acid, although other monomers may be incorporated, and are herein referred to as polyalkenoic acids. See generally, Prosser et al., *Developments in Ionic Polymers*- 1, Chapter 5, Applied Science Publishers (London and New York, 1983). Recently such polymers have been further modified in the laboratory of the assignee of this invention by the incorporation of addition polymerizable reactive groups as mentioned above. Their preparation is described in U.S. Pat. No. 5,130,347.

Preferred polymeric compounds used in the primer of the invention have a weight average molecular weight prior to hardening of more than about 500, although preferably no greater than 2,000,000. More preferably, polymeric compounds for use in the primer have a weight average molecular weight prior to hardening of between about 1,000 and 1,000,000 evaluated against a polystyrene standard using gel permeation chromatography. Most preferably, polymeric compounds for use in the primer have a weight average molecular weight prior to hardening of between about 5,000 and 200,000.

Suitable monomer components in the film former include 2-hydroxyethylacrylate, 2-hydroxyethylmethacrylate ("HEMA"), 2- and 3-hydroxypropylacrylate and methacrylate, 1,3- and 2,3-dihydroxypropylacrylate and methacrylate, 2-hydroxypropyl-1,3-diacrylate and dimethacrylate, 3-hydroxypropyl-1,2-diacrylate and dimethylacrylate, pentaerythritol diacrylate and dimethacrylate, acrylic acid, methacrylic acid, 2-trimethylammonium ethylmethacrylic chloride, 2-acrylamido-2-methylpropane-sulfonic acid, acrylamide, methacrylamide, 2-hydroxyethylacrylamide and methacrylamide, N,N-bis(2-hydroxyethyl)acrylamide and methacrylamide, N-alkyl-N-hydroxyethyl acrylamides and methacrylamides, 2- and 3-hydroxypropylacrylamide and methacrylamide, methacrylamidopropyltrimethylammonium chloride, polyethyleneglycol (400) diacrylate and dimethacrylate, glycerol dimethacrylate and diacrylate, gylcerol monomethacrylate and monoacrylate, pentaerylthritol trimethacrylate and triacrylate, and mixtures thereof. It is expected that where an acrylate monomer is suitable the methacrylate analog will likewise be suitable.

Alternatively, water insoluble or sparingly water soluble components may also be incorporated in useful primers of the present invention. For example tetraethylene glycol dimethacrylate ("TEGDMA"), a sparingly water soluble monomer, may provide excellent priming action. Additionally, some amount of water insoluble components, such as the dimethacrylate derived from the reaction between methacrylic acid and the diglycidyl ether of bisphenol A ("Bis-GMA") may also be incorporated in the present primers with good overall bonding results.

The film former preferably comprises one or more suitable cosolvents. The cosolvent(s) aid in wetting the dental surface (especially when the surface is hard tissue) and in solubilizing or dispersing the substances. Suitable cosolvents include water, alcohols such as methanol, ethanol, 1-propanol, 2-propanol, and 2-methyl-2-propanol, ketones such as acetone and methylethylketone, aldehydes such as formaldehyde, acetaldehyde, propionaldehyde, acrolein, glutaraldehyde and 2-hydroxy-adipaldehyde, amides such as acetamide and N,N-dimethylformamide, and other substances such as tetrahydrofuran and dimethyl sulfoxide. The film former preferably contains less than about 95 weight percent cosolvent, more preferably between about 15 and about 85 weight percent cosolvent.

The primer preferably also is acidic. Acidity may be provided by incorporating an acid or acid precursor in the priming solution, or by providing the film-former with acidic functionality. Preferably, the priming solution has a pH of less than 7.

When the acidity of the primer is provided through incorporation of a separate acid, the acid may preferably be selected from the same acids recited above for use in the acid etch step.

The above discussion on selection of film-former components identifies a number of materials that contain acidic functionality. It will be appreciated by the skilled artisan that selection of these acid functional film-formers is preferred for imparting acidity to the primer solution.

The priming solution may optionally contain other adjuvants such as polymerization catalysts, medicaments, fluoride compounds, indicators, dyes, wetting agents, buffering agents, thixotropes and the like.

The priming solution is applied by appropriate means, such as a dropper, sponge or brush, and should be allowed to stand on the dental surface long enough to provide the desired degree of priming. The standing time will depend upon the film-former employed, the type of dental surface and the time available for carrying out the priming procedure. For priming dentin and enamel, standing times less than about 5 minutes, and preferably about 5 seconds to one minute provide very effective priming, although shorter or longer times can be used if desired.

The priming solution is optionally hardened on the dental surface before subsequent steps are taken. Hardening may be achieved by allowing the priming solution to dry, or optionally polymerizing the film-former. In order to initiate the polymerization reaction, the film-former may comprise polymerization catalysts such as those mentioned in columns 28 and 29 of U.S. Pat. No. 4,539,382 and described in more detail below.

Alternatively, the priming solution may contain one or more suitable photopolymerization initiators that act as a source of free radicals when activated. Such initiators can be used alone or in combination with one or more accelerators and/or sensitizers.

The photoinitator should be capable of promoting free radical crosslinking of the ethylenically unsaturated moiety on exposure to light of a suitable wavelength and intensity. Visible light photoinitiators are preferred. The photoinitiator frequently can be used alone, but typically it is used in combination with a suitable donor compound or a suitable accelerator (for example, amines, peroxides, phosphorus compounds, ketones and alpha-diketone compounds).

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with or without additional hydrogen donors (such as sodium benzenesulfinate, amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source, the thickness of the layer to be exposed to radiant energy, and the extinction coefficient of the photoinitiator. Typically, the photoinitiator components will be present at a total weight of about 0.01 to about 5%, more preferably from about 0.1 to about 5%, based on the total weight of the composition.

After the priming solution is applied to the treated dental surface, a chemically curable dental adhesive is applied to the primed dental surface.

The chemically curable dental adhesive comprises polymerizable components in a formulation that, upon application to the surface to be bonded, initiates a cure reaction that will result in polymerization of the adhesive and bonding of restoratives to the dental surface. This cure reaction takes place without the need to expose the chemically curable dental adhesive to actinic light. Optionally, however, the dental adhesive may additionally contain photoinitiators as described above to assist in curing the adhesive at exposed margins of the amalgam placement. Generally, chemically curable dental adhesives are provided in a two part format wherein one part contains one part of a reactive pair, and the other part the other half of the pair. Optionally, the chemically curable dental adhesive may be provided in a one part formulation or three or more part formulation. Upon mixing, these components react, initiating a polymerization reaction.

A preferred mode for initiation of the polymerization reaction of an ethylenically unsaturated moiety is the incorporation of an oxidizing agent and a reducing agent as a redox catalyst system to enable the dental adhesive to cure via a redox reaction. Various redox systems are described in U.S. Pat. No. 5,154,762, the disclosure of which is expressly incorporated herein by reference.

The oxidizing agent should react with or otherwise cooperate with the reducing agent to produce free radicals capable of initiating polymerization of the ethylenically unsaturated moiety. The oxidizing agent and the reducing agent preferably are sufficiently shelf stable to permit their storage and use under typical dental conditions. The oxidizing agent and the reducing agent should also be present in an amount sufficient to permit an adequate free radical reaction rate. This can be evaluated by combining the ethylenically unsaturated moiety, the oxidizing agent and the reducing agent and observing whether or not a hardened mass is obtained.

Suitable oxidizing agents include persulfates such as sodium, potassium, ammonium and alkyl ammonium persulfates, benzoyl peroxide, hydroperoxides such as cumene hydroperoxide, tert-butyl hydroperoxide, tert-amyl hydroperoxide and 2,5-dihydroperoxy-2,5-dimethylhexane, salts of cobalt (III) and iron (III), hydroxylamine, perboric acid and its salts, salts of a permanganate anion, and combinations thereof. Hydrogen peroxide can also be used, although it may, in some instances, interfere with the photoinitiator, if one is present. The oxidizing agent may optionally be provided in an encapsulated form as described in U.S. Pat. No. 5,154,762.

Preferred reducing agents include ascorbic acid, metal complexed ascorbic acid, cobalt (II) chloride, ferrous chloride, ferrous sulfate, hydrazine, hydroxylamine, oxalic acid, thiourea, tertiary aromatic amines (such as N,N-bis-(2-hydroxyethyl)-p-toluidine, 4-(dimethylamino)-phenethyl alcohol and the like), and aromatic salts of a dithionite, thiosulfate, benzenesulfinate, or sulfite anion.

A preferred dental adhesive is obtained by combining (1) Bis-GMA with (2) a hydrophilic monomer such as HEMA, hydroxypropyl methacrylate, or methacrylic acid. Suitable monomers for use in the dental adhesive include the monomers described above as well as tetrahydrofurfuryl methacrylate, glyceryl-1,3-dimethacrylate, triethyleneglycol dimethacrylate, ethyl methacrylate, n-hexyl methacrylate, polyethyleneglycol dimethacrylate ("PEGDMA"), and 1,6-hexanediol dimethacrylate. Optionally, the dental adhesive may contain polymers of the type described in the discussion of the priming solution above. The dental adhesive can also contain cosolvents of the type described above. Preferably the dental adhesive is copolymerizable with the residual film formed by the primer. If desired, the dental adhesive can contain conventional fillers, and can also contain adjuvants of the type described above.

Other preferred dental adhesives which can be employed with the present invention contain acrylate- or methacrylate-functional polymers and may also contain phosphorous compounds. In such dental adhesives either a single phosphorus compound or a mixture of phosphorus compounds can be used.

If desired, other free-radically polymerizable non-phosphorus-containing compounds can be mixed with the dental adhesive, for example, as a diluent to reduce viscosity or promote wetting. Other suitable free-radically polymerizable compounds include mono- or poly- (e.g., di-, tri- or tetra-functional) acrylates and methacrylates such as methyl acrylate, 2-hydroxyethyl acrylate, triethyleneglycol diacrylate, neopentylglycol diacrylate, hexamethyleneglycol diacrylate, trimethylolpropane triacrylate, pentaerythritol tetraacrylate, polyalkylene glycol mono- and di-acrylates, urethane mono- or poly-functional acrylates, Bisphenol A diacrylates, and the corresponding methacrylates of the above compounds, as well as acrylamides and methacrylamides, vinyl compounds, styrene compounds, and other olefinically unsaturated compounds suitable for use in the oral environment. U.S. Pat. Nos. 4,499,251, 4,515,930, 4,537,940 and 4,539,382 contain an extensive list of such compounds.

In use, an adhesive is applied to the primed dental surface after initiation of the polymerization reaction in an amount effective to bond the restorative to the dental surface. After the chemically curable dental adhesive is applied to the primed dental surface, the dental restorative is applied to the adhesive-coated dental surface. The restorative is prepared in the conventional manner for placement and applied to the adhesive coated surface before the dental adhesive is fully cured. Typically the dental practitioner has sufficient working time after application of a redox curable dental adhesive in which to place the restorative before full curing of the adhesive. This working time varies depending on the redox curable dental adhesive used.

Shear Adhesive Strength Test Method

Adhesion to dentin or enamel was evaluated as follows:

First, teeth (five bovine teeth unless otherwise noted) of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 320 silicon carbide paper-backed abrasive and then Grade 600 silicon carbide paper-backed abrasive on the lapidary wheel. The polished teeth were stored in distilled water, and used for testing within 2 hours after polishing. The polished teeth were removed from the water and dried using a stream of compressed air.

Samples were prepared using the indicated techniques to bond previously prepared 5 mm diameter, 2 mm thick buttons of the indicated material. In the case of metal, porcelain and precured composite buttons, the sample is polished using a Grade 600 silicon carbide paper-backed abrasive mounted on a lapidary wheel, in order to obtain a shiny surface. The polished and dried metal or amalgam surface was sandblasted with aluminum oxide that has an average particle size of 50 microns until the metal or set amalgam surface had a uniform aluminum oxide surface. Porcelain is then silane treated using 3M™ Scotchbond™ Ceramic Primer. Luting cement from the 3M™ Indirect Porcelain System is then applied to all buttons before seating on the intended substrate. Excess luting cement is scraped away after application of pressure to seat the button.

In the case of bonding uncured composite, previously prepared molds made from approximately 2-mm thick "Teflon" sheet with a 5 mm diameter hole were clamped to each prepared tooth so that the central axis of the hole in the mold was normal to the tooth surface. The hole in each mold was filled with dental composite material. It is believed that the choice of restorative might affect the bond strength values obtained for a given adhesive system. For example, some adhesive systems of the present invention provide very strong bonds to hard tissue that are believed to fail at the restorative-adhesive interface or within the restorative and not at the adhesive-hard tissue interface. A higher strength restorative may increase the measured bond strength for these adhesive systems. Therefore, comparisons between different adhesive systems should be made, wherever possible, using similar restorative systems. The teeth and molds were allowed to stand for about 5 minutes at room temperature, then stored in distilled water at 37° C. for 24 hours unless otherwise noted. The molds were then carefully removed from the teeth, leaving a molded button of restorative attached to each tooth.

Adhesive strength was evaluated by mounting the acrylic disk in a holder clamped in the jaws of an "Instron" apparatus with the polished tooth surface oriented parallel to the direction of pull. A loop of wire (about 0.5 mm diameter) was placed around the restorative button adjacent to the polished tooth surface. The ends of the orthodontic wire were clamped in the pulling jaw of the Instron apparatus, thereby placing the bond in shear stress. The bond was stressed until it (or the dentin or button) failed, using a crosshead speed of 2 mm/min.

Shear adhesion to materials other than teeth was evaluated as follows:

First, the substrate to be tested (e.g.., metals, porcelain, set amalgam; ten samples unless otherwise noted) were partially embedded in circular acrylic discs. The exposed portion of each sample was polished flat and parallel to the acrylic disc using Grade 600 silicon carbide paper-backed abrasive mounted on a lapidary wheel, in order to obtain a shiny metal or amalgam surface. During these polishing steps, the surface was continuously rinsed with water. The polished metal or amalgam was removed from the water and dried using a stream of water and oil-free compressed air. The polished and dried metal or amalgam surface was sandblasted with aluminum oxide that has an average particle size of 50 microns until the metal or set amalgam surface had a uniform aluminum oxide surface. For a 5 mm diameter cross-section, this takes about 15 seconds. The sandblasted metal or amalgam was then sonicated in water for 5 minutes so loose alumina was removed. The samples were then removed from the water and dried using an oil and water-free stream of compressed air.

The restorative materials were bonded to the thus prepared surfaces in the same manner as above.

The following examples are offered to aid in understanding of the present invention and are not to be construed as limiting the scope thereof. Unless otherwise indicated, all parts and percentages are by weight. The Copolymer used in these examples, unless otherwise noted, is an ethylenically unsaturated acidic copolymer prepared like the precipitated dry polymer of EXAMPLE 11 of U.S. Pat. No. 5,130,347. The adhesive used in all examples, except as otherwise noted, was a two part curable adhesive, wherein one part contained 0.25% CPQ, 0.38% DHEPT, 0.50% EDMAB, 61,79% BisGMA and 37.08% HEMA. The second part contained 2.1% BPO, 0.093% BHT, 61.13% BisGMA and 36.68% HEMA. Where commercially available products were tested, manufacturer's instructions were followed.

Experimental

EXAMPLE 1

The effect of the selection of etchants in the present system was evaluated for bonding of cured restorative (Z100 restorative, commercially available from 3M) to dentin following the bond strength protocol as defined above. Various etchants were used in combination with a standard treatment composition, which was three percent sodium benzenesulfinate in ethanol, and a standard primer, which was 13.3% Copolymer/39.8% HEMA/46.9% water. Bond strengths are reported in Table I.

TABLE I

| ETCHANT | SHEAR ADHESIVE BOND STRENGTH (kg/cm$^2$) |
|---|---|
| 10% maleic acid with H$_2$O rinse | 104 ± 30 |
| 10% maleic acid-no rinse | 130 ± 37 |
| 35% phosphoric acid with H$_2$O rinse | 124 ± 52 |
| No etch | 0 |
| 35% phosphoric acid-no rinse | 32 ± 27 |

This example shows that the adhesion of cured restorative to dentin was significantly higher for a methodology that included an acid etch step that left no insoluble salts on the surface of the dentin.

EXAMPLE 2

The effect of the selection of components incorporated in the treatment composition for adhesion of precured composite (Z100 restorative, commercially available from 3M) to dentin was evaluated with the use of a standard etchant, which was 35% phosphoric acid with water rinse, and a standard primer which was 13.3% Copolymer/39.8% HEMA/46.9% water. The results of these bond strength evaluations are set forth in Table II.

TABLE II

| TREATMENT COMPOSITION | SHEAR ADHESIVE BOND STRENGTH (kg/cm$^2$) |
|---|---|
| 3% SBS$^1$/water | 171 ± 28 |
| 6% SBS/89% EtOH/5% H$_2$O | 95 ± 66 |
| 9% SBS/83% EtOH/8% H$_2$O | 129 ± 76 |
| 3% SBS/EtOH | 131 ± 61 |
| 3.5% sodium meta bisulfite/H$_2$O | 255 ± 31 |
| 4.5% sodium thio sulfate/H$_2$O | 62 ± 45 |
| 2.3% sodium sulfite/H$_2$O | 139 ± 56 |
| 3.6% DHEPT$^2$/EtOH | 46 ± 30 |
| 3.0% DMAPE$^3$/EtOH | 20 ± 16 |
| 3% DMAPE/Acetone | 118 ± 39 |
| 3.6% DHEPT/Acetone | 18 ± 15 |
| 1% SBS/EtOH | 148 ± 50 |
| 6% DMAPE/EtOH | 46 ± 64 |
| 10% DMAPE/EtOH | 60 ± 35 |
| ethanol (no electron donor)$^4$ | 73 ± 62 |
| 3% SBS/ethanol$^4$ | 161 ± 26 |

$^1$sodium benzenesulfinate
$^2$N,N-bis-(2-hydroxyethyl)-p-toluidine
$^3$4-(dimethylamino)-phenethyl alcohol
$^4$Testing performed on the same day for side-by-side comparison.

This example shows that good bond strengths are achieved using an electron donor in the treatment solution when bonding precured composite buttons to dentin.

EXAMPLE 3

The effect of selection of primers for adhesion of precured composite (Z100 restorative, commercially available from 3M) to dentin was evaluated by the use of various primers with a standard acid etchant, which was a 35% phosphoric acid followed by water rinse, together with a standard treatment composition, which was 3% sodium benzenesulfinate in ethanol. The results of these bond strength evaluations are reported in Table III.

TABLE III

| PRIMER | SHEAR ADHESIVE BOND STRENGTH (kg/cm$^2$) |
|---|---|
| 13.3% Copolymer/39.8% HEMA/46.9% H$_2$O | 111 ± 51 |
| 7% MDP$^1$/42.7% HEMA/50.3% H$_2$O | 152 ± 37 |
| 2.4% phenol/44.9% HEMA/52.9% H$_2$O | 86 ± 65 |
| 0.45% H$_2$O/44.8% HEMA/54.75% H$_2$O | 93 ± 62 |
| 1.5% acetic acid/45.2% HEMA/53.3% H$_2$O | 86 ± 66 |
| 2.9% maleic acid/44.6% HEMA/52.5% H$_2$O | 118 ± 45 |
| 2.3% oxalic acid/44.9% HEMA/52.9% H$_2$O | 80 ± 48 |
| 1.3% nitric acid/45.3% HEMA/53.4% H$_2$O | 129 ± 54 |
| 0.92% HCl/41.7% HEMA/49.1% H$_2$O | 84 ± 49 |
| 2.5% sulfuric acid/44.8% HEMA/52.8% H$_2$O | 40 ± 30 |
| 1% Copolymer/41.3% H$_2$O/48.7% HEMA | 128 ± 38 |
| 13% Copolymer/H$_2$O | 53 ± 30 |
| 13% Copolymer/EtOH | 24 ± 15 |
| 13% Copolymer/43.5% H$_2$O/43.5% EtOH | 78 ± 36 |
| 7% MDP/13% Copolymer/79.6% H$_2$O | 62 ± 48 |
| 50% Copolymer/23.0% HEMA/27.1% H$_2$O | 4 ± 5 |
| 13% Copolymer/39.8% HEMA/46.9% EtOH | 54 ± 27 |
| No Primer | 37 ± 24 |

$^1$methacryloxydecyl phosphate

This example shows that significant adhesion of a precured composite button to dentin is possible using a primer as described for the present method.

EXAMPLE 4

The shear bond strength of the indicated adherends to dentin was evaluated using an experimental system of the present invention (etchant-35% phosphoric acid with water rinse, treatment composition-3% sodium benzenesulfinate/ethanol, primer-13.3% Copolymer/39.8% HEMA/46.9% water). The adhesive contained 2.1% BPO, 0.093% BHT, 61.13% BisGMA and 36.68% HEMA. This system was compared to a commercially available dental adhesive system following the bond strength protocol as defined above.

The non-precious metal contained 1.8% Beryllium, 4–6% molybdenum, 74–78% Nickel and 12–15% Chromium. The semi-precious metal contained 80% Palladium, 1.5% Silver and 2–5% Gold. The precious metal contained 62% Gold, 9% Copper, 25% Silver and 3% Palladium. The precured composite was Z100 (commercially available from 3M). The porcelain was Unitek Crystar Body porcelain.

TABLE IV

| | SHEAR BOND TO DENTIN | |
|---|---|---|
| | Shear Adhesive Bond Strength (kg/cm$^2$) | |
| Adherend | Exptl System | All-Bond 2 |
| Non-Precious metal | 149 ± 56 | 148 ± 46 |
| Semi-Precious metal | 143 ± 20 | 187 ± 26 |
| Precious metal | 218 ± 36 | 231 ± 54 |
| Precured Composite | 131 ± 81 | 124 ± 23 |
| Porcelain | 60 ± 21 | 57 ± 39 |

This example shows that the experimental system of the present invention achieves shear adhesive bond strengths of adherends to dentin that were at least equal to the bond strengths of commercial products. The present invention has advantage of being an easy to use self-curable adhesive system. The All-Bond 2 product requires multiple applications of a primer that must be mixed in the dental office.

EXAMPLE 5

The shear bond strength of the indicated adherends to enamel was evaluated using an experimental system of the present invention (etchant-35% phosphoric acid with rinse, treatment composition 3% sodium benzenesulfinate/ethanol, primer-13.3% Copolymer/39.8% HEMA/46.9% water). The adhesive contained 2.1% BPO, 0.093% BHT, 61.13% Bis-GMA and 36.68% HEMA. This system was compared to a commercially available dental adhesive system following the bond strength protocol as defined above. The adherends were as described in Example 4.

TABLE V

SHEAR BOND TO ENAMEL

| Adherend | Shear Adhesive Bond Strength ($kg/cm^2$) | |
|---|---|---|
| | Exptl System | All-Bond 2 |
| Non-Precious metal | 263 ± 70 | 273 ± 54 |
| Semi-Precious metal | 144 ± 23 | 228 ± 63 |
| Precious metal | 218 ± 36 | 231 ± 54 |
| Precured Composite | 265 ± 77 | 228 ± 39 |
| Porcelain | 181 ± 67 | 153 ± 52 |

This example shows that the experimental system of the present invention achieves shear adhesive bond strengths of adherends to enamel that were at least equal to the bond strengths of commercial products. The present invention has advantage of being an easy to use self-curable adhesive system. The All-Bond 2 product requires multiple applications of a primer that must be mixed in the dental office.

EXAMPLE 6

The shear bond strength of the indicated adherends to porcelain was evaluated using an experimental system of the present invention (etchant-35% phosphoric acid with rinse, treatment composition 3% sodium benzenesulfinate/ethanol, primer-13.3% Copolymer/39.8% HEMA/46.9% water). The adhesive contained 2.1% BPO, 0.093% BHT, 61.13% Bis-GMA and 36.68% HEMA. The adherends were as described in Example 4.

TABLE VI

SHEAR BOND TO PORCELAIN

| Adherend | Shear Adhesive Bond Strength ($kg/cm^2$) |
|---|---|
| Porcelain | 162 ± 32 |
| Non-Precious metal | 191 ± 32 |
| Semi-Precious metal | 193 ± 12 |
| Precious metal | 161 ± 21 |

This example shows that high shear bond strengths may be achieved using the present method when adhering various adherends to porcelain.

EXAMPLE 7

The shear bond strength of the indicated adherends to previously cured composite (Z100 restorative, commercially available from 3M) was evaluated using an experimental system of the present invention (etchant-35% phosphoric acid with rinse, treatment composition 3% sodium benzenesulfinate/ethanol, primer-13.3% Copolymer/39.8% HEMA/46.9% water). The adhesive contained 2.1% BPO, 0.093% BHT, 61.13% BisGMA and 36.68% HEMA. The adherends were as described in Example 4.

TABLE VII

SHEAR BOND TO COMPOSITE

| Adherend | Shear Adhesive Bond Strength ($kg/cm^2$) |
|---|---|
| Precured Composite | 158 ± 30 |
| Porcelain | 202 ± 41 |
| Non-Precious metal | 266 ± 45 |
| Semi-Precious metal | 264 ± 42 |
| Precious metal | 232 ± 55 |

This example shows that high shear bond strengths may be achieved using the present method when adhering various adherends to composites.

EXAMPLE 8

The shear bond strength of the indicated adherends to non-precious metal was evaluated using an experimental system of the present invention (etchant-35% phosphoric acid with rinse, treatment composition 3% sodium benzenesulfinate/ethanol, primer-13.3% Copolymer/39.8% HEMA/46.9% water). The adhesive contained 2.1% BPO, 0.093% BHT, 61.13% BisGMA and 36.68% HEMA. The adherends were as described in Example 4.

TABLE VIII

SHEAR BOND TO NON-PRECIOUS METAL

| Adherend | Shear Adhesive Bond Strength ($kg/cm^2$) |
|---|---|
| Precured Composite | 162 ± 30 |
| Porcelain | 200 ± 69 |
| Non-Precious metal | 308 ± 61 |
| Semi-Precious metal | 301 ± 40 |
| Precious metal | 281 ± 28 |

This example shows that high shear bond strengths may be achieved using the present method when adhering various adherends to non-precious metal.

EXAMPLE 9

The shear bond strength of the indicated adherends to semi-precious metal was evaluated using an experimental system of the present invention (etchant-35% phosphoric acid with rinse, treatment composition 3% sodium benzenesulfinate/ethanol, primer-13.3% Copolymer/39.8% HEMA/46.9% water). The adhesive contained 2.1% BPO, 0.093% BHT, 61.13% BisGMA and 36.68% HEMA. The adherends were as described in Example 4.

TABLE IX

SHEAR BOND TO SEMI-PRECIOUS METAL

| Adherend | Shear Adhesive Bond Strength ($kg/cm^2$) |
|---|---|
| Precured Composite | 121 ± 27 |
| Porcelain | 145 ± 51 |
| Non-Precious metal | 308 ± 61 |

TABLE IX-continued

SHEAR BOND TO SEMI-PRECIOUS METAL

| Adherend | Shear Adhesive Bond Strength (kg/cm$^2$) |
|---|---|
| Semi-Precious metal | 301 ± 40 |
| Precious metal | 281 ± 28 |

This example shows that high shear bond strengths may be achieved using the present method when adhering various adherends to semi-precious metal.

EXAMPLE 10

The shear bond strength of the indicated adherends to precious metal was evaluated using an experimental system of the present invention (etchant-35% phosphoric acid with rinse, treatment composition 3% sodium benzenesulfinate/ethanol, primer-13.3% Copolymer/39.8% HEMA/46.9% water). The adhesive contained 2.1% BPO, 0.093% BHT, 61.13% BisGMA and 36.68% HEMA. The adherends were as described in Example 4.

TABLE X

SHEAR BOND TO PRECIOUS METAL

| Adherend | Shear Adhesive Bond Strength (kg/cm$^2$) |
|---|---|
| Precured Composite | 126 ± 22 |
| Porcelain | 97 ± 19 |
| Non-Precious metal | 133 ± 17 |
| Semi-Precious metal | 147 ± 19 |
| Precious metal | 126 ± 30 |

This example shows that high shear bond strengths may be achieved using the present method when adhering various adherends to precious metal.

EXAMPLE 11

The shear bond strength of the indicated adherends to set amalgam was evaluated using an experimental system of the present invention (etchant-35% phosphoric acid with rinse, treatment composition 3% sodium benzenesulfinate/ethanol, primer-13.3% Copolymer/39.8% HEMA/46.9% water). The adhesive contained 2.1% BPO, 0.093% BHT, 61.13% BisGMA and 36.68% HEMA. The adherends were as described in Example 4. The set amalgam was Disperalloy™ amalgam.

TABLE XI

SHEAR BOND TO SET AMALGAM

| Adherend | Shear Adhesive Bond Strength (kg/cm$^2$) |
|---|---|
| Precured Composite | 123 ± 38 |
| Porcelain | 113 ± 40 |
| Non-Precious metal | 195 ± 54 |
| Semi-Precious metal | 172 ± 53 |
| Precious metal | 136 ± 48 |

This example shows that high shear bond strengths may be achieved using the present method when adhering various adherends to set amalgam.

EXAMPLE 12

The shear bond strength of the indicated adherends to glass ionomer core was evaluated using an experimental system of the present invention (etchant-35% phosphoric acid with rinse, treatment composition 3% sodium benzenesulfinate/ethanol, primer-13.3% Copolymer/39.8% HEMA/46.9% water). The adhesive contained 2.1% BPO, 0,093% BHT, 61.13% BisGMA and 36.68% HEMA. The adherends were as described in Example 4. The glass ionomer core was 3M™ Vitremer™ glass ionomer restorative/core buildup material.

TABLE XII

SHEAR BOND TO GLASS IONOMER CORE

| Adherend | Shear Adhesive Bond Strength (kg/cm$^2$) |
|---|---|
| Precured Composite | 106 ± 34 |
| Porcelain | 185 ± 52 |
| Non-Precious metal | 193 ± 40 |
| Semi-Precious metal | 187 ± 31 |
| Precious metal | 196 ± 39 |

This example shows that high shear bond strengths may be achieved using the present method when adhering various adherends to glass ionomer core.

EXAMPLE 13

The shear bond strength of a self-cure composite material (3M™ P-10™ Resin Bonded Ceramic restorative from 3M) to various dental surfaces was evaluated using an experimental system of the present invention (etchant-35% phosphoric acid with rinse, treatment composition 3% sodium benzenesulfinate/ethanol, primer-13.3% Copolymer/39.8% HEMA/46.9% water). This system was compared to a commercially available dental adhesive system following the bond strength protocol as defined above. The adherends were as described in Example 4.

TABLE XIII

SHEAR BOND OF COMPOSITE TO VARIOUS DENTAL SURFACES

| Dental Surface | Exptl System | All-Bond 2 |
|---|---|---|
| Dentin | 179 ± 39 | 136 ± 38 |
| Enamel | 278 ± 69 | 253 ± 52 |
| Porcelain | 135 ± 34 | 154 ± 15 |
| Composite | 191 ± 27 | 187 ± 76 |
| Non-Precious Metal | 139 ± 29 | 183 ± 83 |
| Semi-Precious Metal | 108 ± 40 | 181 ± 59 |
| Precious Metal | 123 ± 49 | 90 ± 42 |
| Set Amalgam | 131 ± 30 | 153 ± 34 |

This example shows that high shear bond strengths may be achieved using the present method when adhering composite material to various dental surfaces. The set amalgam was Disperalloy™ amalgam.

EXAMPLE 14

To show the use of alternative adhesive components, adhesion of a precured composite button was carried out as in Example 4 with the following adhesive components:

Part A-0.25% CPQ, 0.38% DHEPT, 0.50% EDMAB, 61,79% BisGMA and 37.08% HEMA.

Part B-2.1% BPO, 0.093% BHT, 61.13% BisGMA and 36.68% HEMA.

TABLE XIV

| ADHESIVE SYSTEM | SHEARBOND STRENGTH kg/cm$^2$ |
| --- | --- |
| Part A & B | 155 ± 52 |
| Part B only | 147 ± 76 |
| Part A only | 122 ± 16 |

This example shows that high shear bond strengths may be achieved using the present method when adhering composite material to dentin using various combinations of adhesive components.

What is claimed:

1. A method for adhering a non-amalgam dental restorative to a dental surface comprising, in order, the steps of
   a) etching said dental surface with acid,
   b) applying a treatment composition comprising an electron donor compound to said etched dental surface, thereby providing a treated dental surface,
   c) applying a priming solution containing a film-former to said treated dental surface, thereby providing a primed dental surface,
   d) applying a chemically curable dental adhesive to said primed dental surface thereby providing an adhesive-coated dental surface, and
   e) applying a non-amalgam dental restorative to said adhesive-coated dental surface; wherein said electron donor compound is selected such that the dental restorative has a higher Adhesive Shear Bond Strength than a like method without said electron donor compound.

2. The method of claim 1, wherein said dental surface is hard tissue.

3. The method of claim 2, wherein said hard tissue is dentin.

4. The method of claim 2, wherein said hard tissue is enamel.

5. The method of claim 1, wherein said dental surface is porcelain.

6. The method of claim 1, wherein said dental surface is previously placed amalgam.

7. The method of claim 1, wherein said dental surface is metal.

8. The method of claim 1, wherein said treatment composition comprises sodium benzenesulfinate.

9. The method of claim 8, wherein said treatment composition comprises water.

10. The method of claim 1, wherein said priming solution comprises an acid having a pKa of less than about 10.

11. The method of claim 1, wherein said priming solution comprises HEMA.

12. The method of claim 1, wherein said priming solution comprises polyalkenoic acid copolymer.

13. The method of claim 1, wherein said chemically curable dental adhesive comprises a redox polymerization initiator system.

14. The method of claim 1, wherein said restorative is a dental composite restorative.

15. The method of claim 1, wherein said adhered dental restorative exhibits a Shear Adhesive Strength to dentin greater than about 30 kg/cm$^2$.

16. The method of claim 1, wherein said adhered dental restorative exhibits a Shear Adhesive Strength to dentin greater than about 60 kg/cm$^2$.

* * * * *